(12) United States Patent
Bastia et al.

(10) Patent No.: US 8,894,572 B2
(45) Date of Patent: Nov. 25, 2014

(54) DEVICE FOR EXAMINING AND SURGICALLY OPERATING ON BODY CAVITIES, IN PARTICULAR THE ANAL AND VAGINAL CAVITIES

(75) Inventors: Filippo Bastia, Carpi (IT); Pier Paolo Dal Monte, Pianoro (IT)

(73) Assignee: THD S.p.A., Correggio (IT)

( * ) Notice: Subject to any disclaimer, the term of this patent is extended or adjusted under 35 U.S.C. 154(b) by 1016 days.

(21) Appl. No.: 12/442,307

(22) PCT Filed: Sep. 21, 2006

(86) PCT No.: PCT/IT2006/000674
§ 371 (c)(1),
(2), (4) Date: Mar. 20, 2009

(87) PCT Pub. No.: WO2008/035384
PCT Pub. Date: Mar. 27, 2008

(65) Prior Publication Data
US 2010/0041954 A1    Feb. 18, 2010

(51) Int. Cl.
*A61M 29/00* (2006.01)
*A61B 1/32* (2006.01)
*A61B 1/303* (2006.01)
*A61B 1/31* (2006.01)

(52) U.S. Cl.
CPC . *A61B 1/32* (2013.01); *A61B 1/303* (2013.01); *A61B 1/31* (2013.01)
USPC .......................................... 600/210; 600/235

(58) Field of Classification Search
CPC .......... A61B 1/303; A61B 1/307; A61B 1/31; A61B 1/32; A61B 17/42; A61B 17/02; A61B 17/267; A61B 17/3429; A61B 17/00008; A61B 17/0206; A61B 17/0293; A61B 17/3423; A61B 17/0218; A61B 2017/3452; A61B 2017/345; A61B 2017/346; A61B 1/267

USPC ......... 606/108, 119, 190, 191, 193, 196, 197, 606/205, 207; 600/101–106, 114, 127–130, 600/133, 135, 138, 170, 171, 176, 183–185, 600/188, 190–206, 208, 210–225, 231, 233, 600/235, 237, 239, 242, 243, 244, 245
See application file for complete search history.

(56) References Cited

U.S. PATENT DOCUMENTS 877,618 A * 1/1908 Van Orden .................... 600/184
2,469,880 A * 5/1949 Kowan .......................... 600/184
(Continued)

FOREIGN PATENT DOCUMENTS

DE    3907072 C1    3/1990
EP    1183991 A2    3/2002
(Continued)

*Primary Examiner* — Pedro Philogene
*Assistant Examiner* — Lynnsy Summitt
(74) *Attorney, Agent, or Firm* — Pearne & Gordon LLP

(57) ABSTRACT

The device for examining and surgically operating on body cavities, in particular the anal and vaginal cavities, comprises an elongate hollow body (2) exhibiting an insertion portion (3) for at least a partial insertion of the device (1) internally of the cavity and an open portion (4), through which the doctor or surgeon can operate. The hollow body (2) exhibits a longitudinal window (5) through which the pathological site of interest on the cavity wall can be isolated. The hollow body (2) exhibits, along the longitudinal window, a transversal section constituted by a curved sector, ends of which extend in a substantially parallel directions which diverge in such a way as to stretch the affected portion of cavity without invading the viewing space and/or the maneuvering space defined by the hollow body (2).

20 Claims, 3 Drawing Sheets

(56) References Cited

U.S. PATENT DOCUMENTS

| | | | |
|---|---|---|---|
| 5,456,699 A * | 10/1995 | Armstrong | 606/108 |
| 6,033,361 A * | 3/2000 | Co et al. | 600/210 |
| 6,042,538 A * | 3/2000 | Puskas | 600/114 |
| 6,080,102 A * | 6/2000 | Konou et al. | 600/114 |
| 6,142,933 A * | 11/2000 | Longo et al. | 600/184 |
| 6,206,822 B1 * | 3/2001 | Foley et al. | 600/114 |
| 6,428,473 B1 * | 8/2002 | Leonard et al. | 600/219 |
| 6,432,045 B2 * | 8/2002 | Lemperle et al. | 600/135 |
| 6,616,603 B1 * | 9/2003 | Fontana | 600/199 |
| 2003/0163026 A1 | 8/2003 | Fontana | |
| 2006/0287583 A1 * | 12/2006 | Mangiardi | 600/208 |

FOREIGN PATENT DOCUMENTS

| | | |
|---|---|---|
| FR | 2668357 A2 | 4/1992 |
| WO | 01 21060 A1 | 3/2001 |
| WO | 0160238 A1 | 8/2001 |
| WO | 2006064247 A2 | 6/2006 |

* cited by examiner

DEVICE FOR EXAMINING AND SURGICALLY OPERATING ON BODY CAVITIES, IN PARTICULAR THE ANAL AND VAGINAL CAVITIES

TECHNICAL FIELD

The invention relates to a device for examining and surgically operating on body cavities, in particular the anal and vaginal cavities.

The invention relates to the medical/surgical field, and in particular concerns inspections and/or surgical operations on body cavities, such as the anal and vaginal cavities.

In particular, the invention is usefully applied in inspecting and/or surgically treating coloproctological pathologies, such as for example haemorrhoids, anal fissures, recto-vaginal fistulas, papillomas, rectoceles, anal cancers, fibrous polyps, hypertrophic anal papillomas, rectal prolapse, ulcerous rectocolitis, Crohn's disease, polyposis, colorectal tumours and the like.

BACKGROUND ART

As is known, inspection and/or surgical treatment of anal and/or vaginal orifices which are suffering from a pathological condition normally requires the use of devices which open the cavity, allowing visual inspection to be performed as well as offering accessibility to one or more surgical instruments.

These devices normally exhibit a hollow elongate body predisposed to be inserted into the cavity.

Generally the hollow body exhibits an open end for insertion of the surgical instruments needed for the operation. At the open end, the hollow body is provided with a handle gripped by the doctor during diagnostic examinations, or by the surgeon undertaking the operation.

In certain cases the handle also functions as a housing body for a light source for illuminating the inside of the anal and/or vaginal canal.

With particular reference to some coloproctological pathologies, the main surgical intervention techniques which include use of divaricators, such as the ones mentioned above, are based on the removal of tissue, i.e. the surgical removal of the portions of rectal mucosa which are affected by the pathology. In these techniques the removal of haemorrhoidal prolapse is possible together with the suturing of the cut zones, as described and illustrated in WO 01/21060.

In this case, the divaricator accessory used for the surgical intervention exhibits a hollow body developing longitudinally in an open semi-cylindrical conformation.

In the above prior art, the hollow body exhibits two open opposite ends.

A first end is predisposed to be inserted internally of the respective cavity, and a second end is predisposed to remain external of the cavity in order to enable the surgeon to introduce all the instruments necessary for the operation.

The hollow body is insertable in the cavity by means of an anatomical cone-shaped introducer. In this way the hollow body is made to slide longitudinally with respect to the anatomical cone-shaped introducer internally of the patient's body.

At the open introductory end, the hollow body also exhibits an opening or window for intercepting a part of the haemorrhoidal prolapse and for enabling extrusion thereof for subsequent removal and suture thereof by means of the appropriate surgical instruments.

In order to enable a sufficient space in which to work, the accessory divaricator device exhibits, in transversal section, a semi-circular development which enables partial divarication of the cavity at the part interested by the pathology.

Also known in the prior art, and as described in document EP1183991, are divaricator devices the hollow body of which, presenting an elongate conformation, exhibit an insertion end which is closed and an opposite end which is open and through which it is possible to reach the interested portion of body cavity. In this case, in transversal section the hollow body exhibits a substantially circular profile, interrupted according to an arc of circumference the length of the span of which is shorter than the diameter of the profile itself. In other words, the transversal section of the hollow body exhibits a substantially C-shaped profile the terminal portions of which converge to constitute respective support and/or rest arches for angular portions of the wall of the body cavity under examination.

The present applicant has noted that known-type divaricator devices are not free of some drawbacks, principally in relation to the effectiveness thereof in terms of divarication of the cavity during the stage of diagnostic examination and/or surgical operation in patients exhibiting notable muscle hypotone or in patients affected, for example by rectoceles or by similar pathologies.

In particular, it has been seen that in cases of patients with muscle hypotone in the sphincter or in perineal zones not having muscular tissue, for example the female perineal zone interpositioned between the anal cavity and the vaginal cavity, the tissue interested by a pathology tends to sag, invading the space delimited by the hollow body of the divaricator. From the diagnostic point of view this leads to greater difficulty in completely viewing and examining the pathology, and from the surgical point of view means the operation site is not sufficiently free for necessary manoeuvres.

This disadvantage is encountered both during use of a divaricator like the one illustrated in FIG. 1, which in transversal section exhibits a semicircular profile, and during the use of a divaricator as illustrated in FIG. 2, which is substantially C-shaped. In the first case (FIG. 1) the sagging and/or the pathological tissue significantly invades the space delimited by the hollow body. In the second case (FIG. 2) the sagging tissue and/or the pathological tissue is slightly supported by terminal portions of the transversal section of the hollow body, but nonetheless falls internally thereof across the interrupted part of the section thereof.

Also noteworthy is the fact that none of the above-described devices enables the surgeon to localise and circumscribe the operation zone for treatment of the pathology.

From the anatomical point of view, the initial longitudinal section of the human anal canal includes a first portion, about 2.5-3 cm deep, called the anatomical anal canal, and a second portion, about 5-5 cm deep, known as the surgical anal canal.

The two portions are subdivided by a line of folds known as Morgagni's rectal columns.

The fold line delimits the pain threshold as below it a surgical intervention is better avoided as it causes very great pain to the patient upon waking from the anaesthetic, while above the line operations can be performed without causing the patient discomfort; it is for this reason that this second portion is called the surgical anal canal.

The prior-art devices exhibit a longitudinal window over the whole length of the hollow body, and therefore do not isolate the part to be treated.

Indeed, the anal tissue that falls into the hollow body belongs both to the first portion, which does not necessarily have to be surgically treated, and for the second portion.

In certain cases the first portion can even obscure the second portion i.e. the part to be surgically treated.

The applicant has therefore found that in order to safeguard the patient it is advisable to protect this area, in order to prevent the surgical instruments, for example needles, from accidentally causing lesions in the tissue of the first portion, as well as to prevent the tissue from those zones' limiting the operativity of the surgeon by invading the operational area.

The present invention is therefore aimed at providing a device for examination or surgical operation on body cavities, in particular anal and/or vaginal cavities, which obviates the above-cited drawbacks in the prior art.

A fundamental aim of the invention is to provide a device for examining and/or surgically operating on the anal and/or vaginal cavities which device leaves the visual field afforded by the device and the operating space for the hollow body of the device free.

A further aim of the present invention is to provide a device for examination of and/or surgical operation on the cavities which can circumscribe the intervention zone for treatment of the pathology.

A further aim of the present invention is to prevent hypotonic soft tissues and/or anal pathologies of the anal or vaginal cavities from invading the internal space of the hollow body of the device.

The set aims and more besides are all attained by a device for inspection or surgical intervention of body cavities, in particular anal and/or vaginal cavities, as specified in the appended claims.

DISCLOSURE OF INVENTION

There now follows, by way of non-exclusive example, a description of a preferred embodiment of a device for examination or surgical intervention on body cavities, in particular anal and/or vaginal cavities, in accordance with the accompanying figures of the drawings, in which.

With reference to figures from 3 to 8, 1 denotes in its entirety a device for examination or surgical intervention on body cavities, in particular anal and/or vaginal cavities, in accordance with the present invention.

As is evident in figures from 3 to 5, the device comprises a hollow body 2 having a substantially elongate shape and exhibiting an insertion portion 3 for at least partial insertion of the device 1 internally of a cavity A which can be either anal or vaginal, and an open portion 4, arranged on an opposite side with respect to the insertion portion 3, through which the cavity A is at least partially visible or reachable by at least a surgical instrument.

In order to enable easy insertion of the device 1 in the cavity A to be examined and/or to be surgically operated upon, while at the same time preventing an exit of organic material, for example faeces or the like, the insertion portion 3 is substantially closed and rounded, and preferably tapered.

Figure 5:
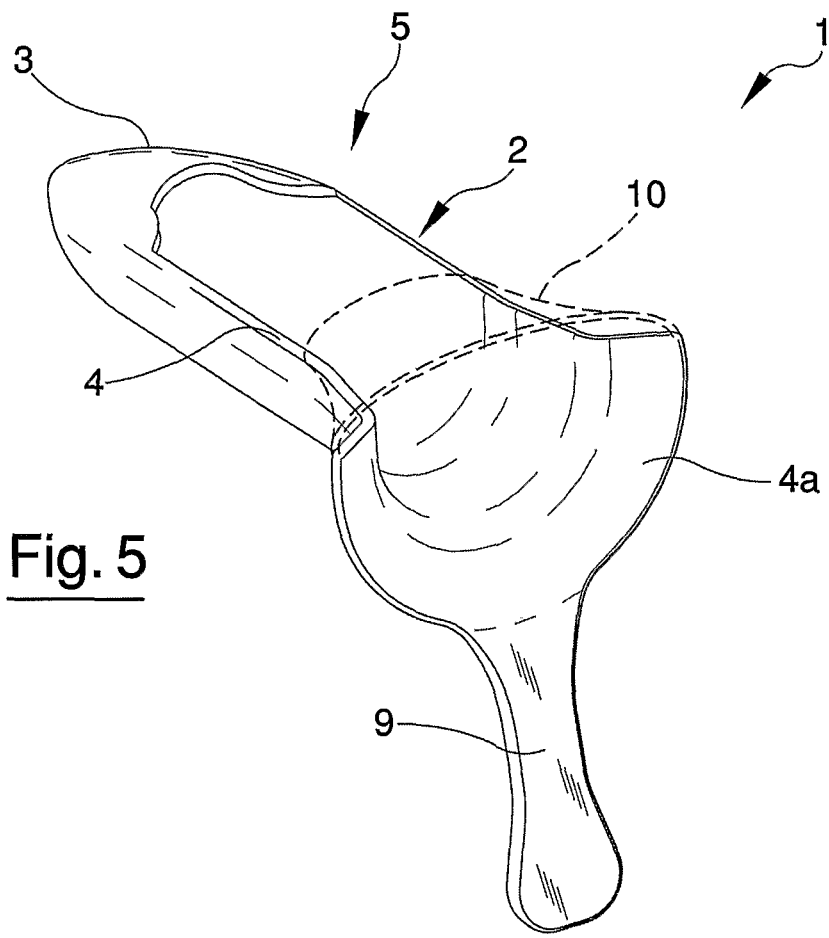
FIG. 5 is a perspective view of a device for examination or surgical intervention on body cavities, in accordance with a second embodiment of the present invention.
Figure 3:
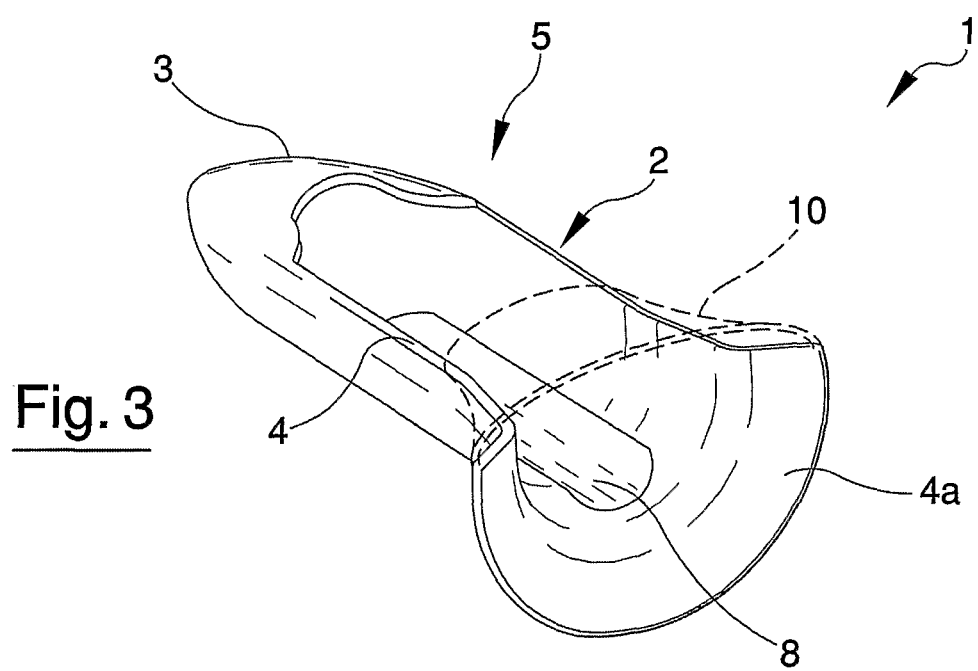
FIG. 3 is a perspective view of a device for examination or surgical intervention on body cavities, in particular the anal and/or vaginal cavities, in accordance with a first embodiment of the present invention.

With reference to FIGS. 3 and 5, the hollow body 2 narrows towards the insertion portion 3 and broadens towards the open end 4 at which open end 4 the hollow body 2 exhibits a truncoconical portion 4a predisposed to rest on the body of a patient at the peripheral zone of the cavity A to be examined and/or surgically treated.

As can be seen in FIGS. 3 and 5, the hollow body 2 exhibits a longitudinal window 5 for inspection and/or intervention through which the pathological situation to be treated can be isolated. The longitudinal window 5 develops between the open portion 4 and the insertion portion 3, preferably without being part of either one.

In more detail, as can be seen in FIGS. 3 and 5, the longitudinal window 5 starts downstream of the insertion portion 3 and terminates upstream of the open portion 4, being thus closed and entirely contained between the two portions 3, 4.

Figure 4:
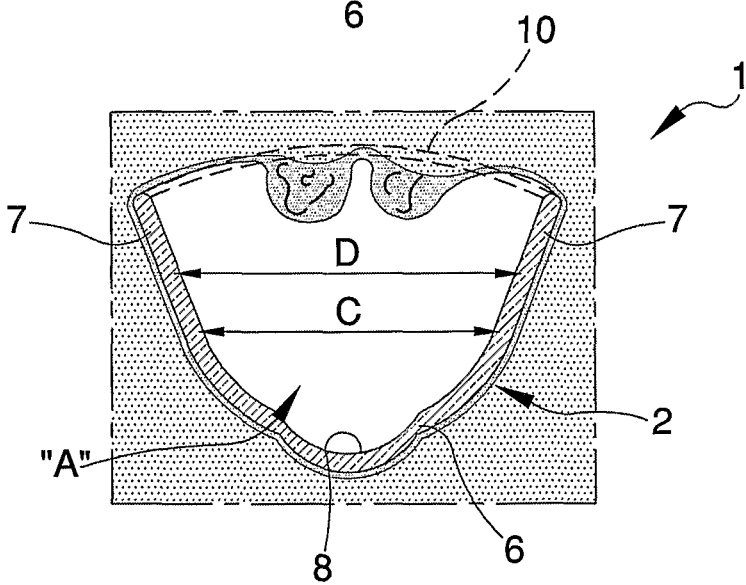
FIG. 4 is a transversal section of the device of claim 3.

With reference to FIGS. 4 and from 6 to 8, at least a longitudinal portion of the hollow body 2, corresponding to the longitudinal window 5, exhibits, in transversal section, a structural sector 6 which extends in a curve, and is preferably semicircular.

The structural sector 6 advantageously exhibits opposite ends 7 which extend in non-converging directions so as to divaricate the cavity while at the same time maintaining the portion of cavity A affected by the pathology at a tension which is sufficient for it to be viewed and/or treated.

In particular, the distance D between the ends 7 of the structural sector 6 of the hollow body 2 is greater than or equal to a reference span C of the curved development of the structural sector 6, which span C is longer than any other span which can be traced across the same curved profile.

In the present embodiment of substantially semi-circular structural sectors 6, the maximum span C corresponds to the diameter of the semicircular profiles, for which reason the distance D between the two ends 7 of the respective structural sectors 6 is greater than or equal to the respective maximum spans C.

Figure 1:
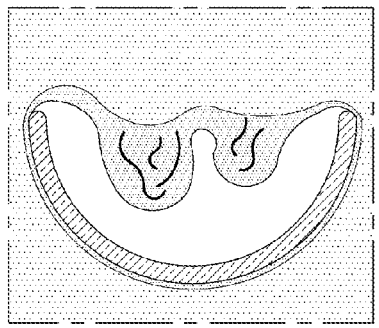
FIG. 1 is a transversal section of a device for examination or surgical intervention on the anal cavity according to a first solution in the prior art.
Figure 2:
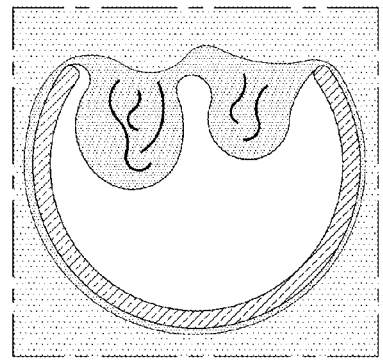
FIG. 2 is a transversal section of a device for examination or surgical intervention on the anal cavity according to a second solution in the prior art.
Figure 6:
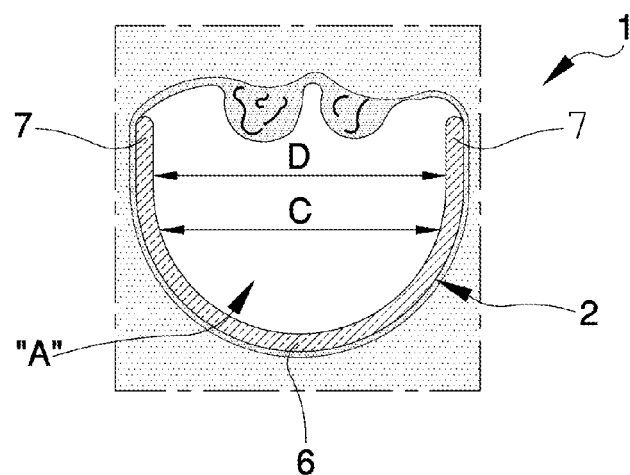
FIG. 6 is a transversal section of a device for examination or surgical intervention on body cavities, in accordance with a third embodiment of the present invention.

With reference to the embodiment illustrated in FIG. 6, the ends 7 of the structural sector 6 of the hollow body develop in divergent directions.

With reference to the embodiments illustrated in FIGS. 4 and from 7 to 9, the ends 7 of the structural sector 6 of the hollow body 2 develop in substantially diverging directions.

Figure 7:
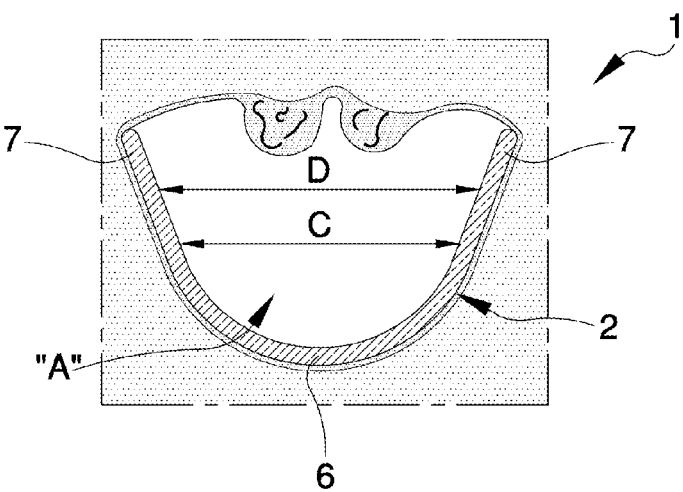
FIG. 7 is a transversal section of a device for examination or surgical intervention on body cavities, in accordance with a fourth embodiment of the present invention.

With reference to the embodiment represented in FIGS. 4 and 7, the ends of the structural sector 6 of the hollow body 2 develop in diverging straight directions.

Figure 8:
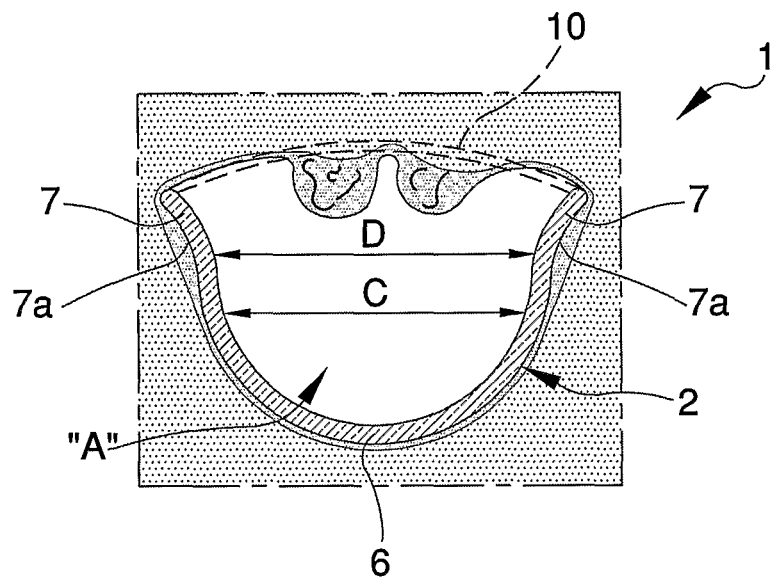
FIG. 8 is a transversal section of a device for examination or surgical intervention on body cavities, in accordance with a fifth embodiment of the present invention.
Figure 9:
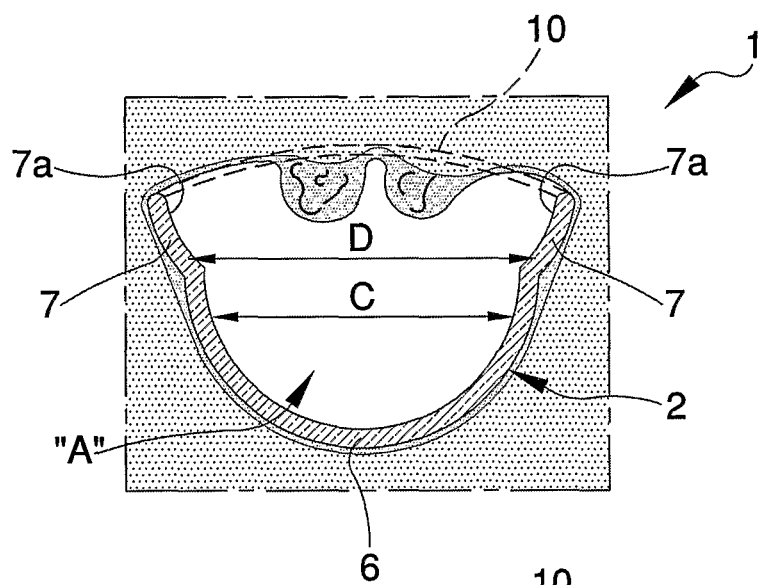
FIG. 9 is a transversal section of a device for examination or surgical intervention on body cavities, in accordance with a sixth embodiment of the present invention.

With reference to the embodiments represented in FIGS. 8 and 9, each end 7 of the structural sector 6 of the hollow body 2 has a curved transversal section.

In the embodiment illustrated in FIG. 8, the curved ends 7 of the structural sector 6 exhibit concavities 7a which face in opposite directions, each towards an outside of the hollow body 2.

In the embodiment of FIG. 9, the curved ends 7 of the structural sector 6 exhibit concavities 7a which at least partially face one another. In other words, the concavities 7a of the curved ends 7 face a median plane interpositioned between the ends 7.

Still with reference to FIG. 9, the curved ends 7 of the structural sector 6 are at least partially opposite-facing with respect to the structural sector 6 in such a way as at least partially to face the pathological site to be examined and/or surgically treated.

With reference to the appended FIGS. 3 and 5, the ends 7 each exhibit an initial tract, which intersects the open portion 4, connected to each other via a preferably convex bridge 10.

The bridge inferiorly delimits the closed longitudinal window 5.

The hollow body 2 internally exhibits at least a channel 8 for facilitating and permitting a manoeuvring of a diagnostic and/or surgical instrument which is necessary for the type of intervention being performed.

The channel 8 is advantageously afforded at least partially along the longitudinal development of the hollow body 2.

With reference to the embodiment of FIG. 5, the device 1 is further provided with a handle 9 which can be gripped manually in order to orient and displace the device simply and precisely during the examination and/or surgical operation. The handle 9 is solidly constrained to the hollow body 2 at the open portion 4 thereof and is at an opposite side thereof to the longitudinal window 5.

The invention solves the problems encountered in the prior art and offers important advantages.

Firstly, the above-described device is well designed for diagnostic examinations and/or surgical operations in relation to various pathologies which interest the anal and/or vaginal cavities.

Also, the device can permit viewing, isolating and/or reaching the area affected by the pathology following an obvious procedure and avoiding obstacles, even in situations where there is muscle hypotone and/or pathologies which soften the surrounding tissues of the cavities, causing them to droop or sag.

Advantageously the arranging of a hollow body which in transversal section exhibits substantially parallel or diverging development enables the interested portions of cavity to be tensed, which keeps the affected area in the zone of the longitudinal window of the hollow body.

Further, the presence of the bridge 10 at the open zone 4 prevents the part of the anal cavity which is not involved with the surgical operation from falling into the inside of the hollow body 2.

In this way the space for manoeuvring and viewing is free and delimited, facilitating the work of the doctor or surgeon in the diagnostic and/or surgical treatment operations.

The invention claimed is:

1. A device for examining and surgically operating on anal and vaginal cavities, comprising an elongate hollow body exhibiting a closed insertion portion for at least a partial insertion of the device internally of the cavity and an open portion, arranged on an opposite side to the insertion portion, through which the cavity is at least partially visible or reachable by at least a surgical instrument, the device further comprising a handle protruding from the hollow body at said open portion, the handle being adapted to be gripped manually in order to orient and displace the device, at least a part of the hollow body exhibiting, in transversal section, a structural sector extending in a substantially curved development, wherein the structural sector exhibits, in transversal section, opposite ends which develop in diverging directions, wherein a distance between said opposite ends of the structural sector is greater than a reference span of the curved development of the structural sector which reference span is longer than other spans which can be identified in the same curved profile development, the structural sector comprising a wall which extends continuously from one end to another end of said opposite ends, said wall extending from the closed insertion portion up to the open portion, wherein each end of the structural sector of the hollow body exhibits, in transversal section, a straight development.

2. The device of claim 1, wherein the hollow body internally exhibits at least a channel for manoeuvring at least a diagnostic and/or a surgical instrument.

3. The device of claim 2, wherein the channel is at least partially afforded along the elongate development of the hollow body.

4. The device of claim 1, wherein the insertion portion is rounded.

5. The device of claim 4, wherein the insertion portion is tapered.

6. The device of claim 1, wherein the hollow body exhibits a closed longitudinal window.

7. The device of claim 6, wherein the longitudinal window develops downstream of the insertion portion and terminates upstream of the open portion.

8. The device of claim 6, wherein the ends exhibit a bridge at the open portion, which bridge joins the ends.

9. The device of claim 8, wherein the bridge inferiorly delimits the longitudinal window.

10. The device of claim 8, wherein the bridge is convex.

11. A device for examining and surgically operating on anal and vaginal cavities, comprising an elongate hollow body exhibiting a closed insertion portion for at least a partial insertion of the device internally of the cavity and an open portion, arranged on an opposite side to the insertion portion, through which the cavity is at least partially visible or reachable by at least a surgical instrument, the device further comprising a handle protruding from the hollow body at said open portion, the handle being adapted to be gripped manually in order to orient and displace the device, at least a part of the hollow body exhibiting, in transversal section, a structural sector extending in a substantially curved development, wherein the structural sector exhibits, in transversal section, opposite ends which develop in diverging directions, wherein a distance between said opposite ends of the structural sector is greater than a reference span of the curved development of the structural sector which reference span is longer than other spans which can be identified in the same curved profile development, the structural sector comprising a wall which extends continuously from one end to another end of said opposite ends, said wall extending from the closed insertion portion up to the open portion, wherein each end of the structural sector of the hollow body exhibits, in transversal section, a curved development and wherein the ends of the structural sector of the hollow body exhibit concavities facing opposite sides, each concavity facing externalwise of the hollow body.

12. The device of claim 11, wherein the hollow body internally exhibits at least a channel for manoeuvring at least a diagnostic and/or a surgical instrument.

13. The device of claim 12, wherein the channel is at least partially afforded along the elongate development of the hollow body.

14. The device of claim 11, wherein the insertion portion is rounded.

15. The device of claim 14, wherein the insertion portion is tapered.

16. The device of claim 11, wherein the hollow body exhibits a closed longitudinal window.

17. The device of claim 16, wherein the longitudinal window develops downstream of the insertion portion and terminates upstream of the open portion.

18. The device of claim 16, wherein the ends exhibit a bridge at the open portion, which bridge joins the ends.

19. The device of claim 18, wherein the bridge inferiorly delimits the longitudinal window.

20. The device of claim 18, wherein the bridge is convex.

* * * * *